(12) United States Patent
Ito et al.

(10) Patent No.: US 6,817,317 B2
(45) Date of Patent: Nov. 16, 2004

(54) ANIMAL PAPILLA DISINFECTANTS AND METHOD OF IMPROVING MICROBIAL ENVIRONMENT

(75) Inventors: Naoki Ito, Tokyo (JP); Eizo Ito, Tokyo (JP)

(73) Assignee: Shinei Fermentec Corporation (JP)

( * ) Notice: Subject to any disclaimer, the term of this patent is extended or adjusted under 35 U.S.C. 154(b) by 134 days.

(21) Appl. No.: 10/344,247

(22) PCT Filed: Aug. 10, 2001

(86) PCT No.: PCT/JP01/06911
§ 371 (c)(1),
(2), (4) Date: Feb. 5, 2003

(87) PCT Pub. No.: WO02/13839
PCT Pub. Date: Feb. 21, 2002

(65) Prior Publication Data
US 2004/0031447 A1 Feb. 19, 2004

(51) Int. Cl.$^7$ .............................................. A01K 29/00

(52) U.S. Cl. ........................ 119/651; 119/652; 119/665; 119/670; 119/672

(58) Field of Search ................................ 119/651, 652, 119/665, 672, 670

(56) References Cited

U.S. PATENT DOCUMENTS

| | | | | |
|---|---|---|---|---|
| 4,653,433 A | * | 3/1987 | Comparetti | 119/672 |
| 5,366,732 A | * | 11/1994 | Zighelboim R | 119/670 |
| 5,415,130 A | * | 5/1995 | Brackett | 119/670 |
| 5,447,122 A | * | 9/1995 | Cortner, Jr. | 119/672 |
| 5,673,650 A | * | 10/1997 | Mottram et al. | 119/670 |
| 6,107,344 A | * | 8/2000 | Loosemore | 514/635 |
| 6,264,967 B1 | * | 7/2001 | Ito et al. | 424/404 |
| 6,550,420 B1 | * | 4/2003 | Bjork | 119/651 |
| 2003/0024484 A1 | * | 2/2003 | Schneider | 119/651 |

OTHER PUBLICATIONS

XP–000990760 "Brachybacterium faecium gen. nov., sp. nov., a Coryneform Bacterium from Poultry Deep Litter" by Matthew D. Collins, Jonathan Brown and Dorothy Jones, pp. 45–48, International Journal of Systematic Bacteriology, Jan. 1998.

XP–000990757 "Taxonomic Study of the Genus Brachybacterium: Brachybacterium nesterenkovii sp. nov." by O.R. Gvozdyak, T.M. Nogina and P. Schumann, pp. 74–78, International Journal of Systematic Bacteriology, Jan. 1992.

XP–000990718 Taxonomic Study of the Genus Brachybacterium: Proposal of Brachybacterium conglomeratum sp. nov., nom. rev., Brachybacterium paraconglomeratum sp. nov., and Brachbacterium rhamnosum sp. nov. by Mariko Takeuchi, Cheng–Xiang Fang and Akira Yokota, pp. 160–168, International Journal of Systematic Bacteriology, Jan. 1995.

XP–000990759 Two Coryneform Bacteria Isolated from the Surface of French Gruyére and Beaufort Cheeses Are New Species of the Genus Brachybacterium: Brachybacterium alimentarium sp. nov. and Brachybacterium tyrofermentans sp. nov., by Karin Schubert, Wolfgang Ludwig, Nina Springer, Reiner Michael Kroppenstedt, Jean–Pierre Accolas and Franz Fiedler, pp. 81–87, International Journal of Systematic Bacteriology, Jan. 1996.

* cited by examiner

Primary Examiner—Charles T. Jordan
Assistant Examiner—Elizabeth Shaw
(74) Attorney, Agent, or Firm—Renner, Kenner, Greive, Bobak, Taylor & Weber

(57) ABSTRACT

This invention provides a novel disinfectant for teats of animals using a microorganism. The disinfectant for teats of animals of this invention is characterized in that it comprises a microorganism belonging to genus Brachybacterium. It is preferable to use a novel microorganisms, which is deposited as a bacterial strain AAA-a of the genus Brachybacterium (Accession No. FERM BP-6848) in the International Depositary Authority.

8 Claims, 2 Drawing Sheets

Change of the feature of bacterial strain AAA-a of genes Brachybacterium cultured for 24 hours (x 2,000)

Change of the feature of bacterial strain AAA-a of genes *Brachybacterium* cultured for 4 hours (x 2,000)

Change of the feature of bacterial strain AAA-a of genes *Brachybacterium* cultured for 24 hours (x 2,000)

ANIMAL PAPILLA DISINFECTANTS AND METHOD OF IMPROVING MICROBIAL ENVIRONMENT

TECHNICAL FIELD

The present invention concerns to a disinfectant for teats of animals, and a method for improving microorganism-environment harmful for animals.

BACKGROUND ART

The disinfection of teats of milking animals, in particular dairy cattle is a most important one of measures for prevention of mastitis. One disinfectant for teats has been developed in UK by Odd et al. in 1952, and has been since used in many countries. In Japan, such disinfectant has been used as a government project for improvement of milk quality since approximately 1975, which is at the present time employed in about 40% of Japanese total dairy cattle.

The method for disinfection of teats of milking cattle that is commonly carried out, includes dipping teats in medical fluid containing such disinfectant as described above to pasteurize or sterilize mastitis-causing bacteria deposited onto the surface of teat skin (namely, post-dipping), and employing wetting agent to improve the status of teat skin such as cracks, whereby inhibiting the growth of bacterium on the surface of teat and preventing mastitis. A number of such disinfecting preparations are currently sold in the market.

However, in the investigation accomplished by the National Institute for Research in Dairying in USA, it is reported that although new infection are decreased by 50% during the period of 12 months in milking cattle population which undergo post-dipping, such decrease of infection is only 14% in a group of cattle which have already infected, and thus subclinical infection by pre-existing mastitis-causing bacteria is likely to be sustained. Namely, although the post-dipping treatment decreases the rate of fresh infection, it is unable to be expected that preventive effects against mastitis-causing bacteria for what is called environmental mastitis is obtained.

The word "environmental mastitis" is meant by mastitis which is developed with occasion or the like in that mastitis-causing bacterium which has deposited onto teat skin and migrated to teat tip penetrates into teat cistern through teat orifice, based on counter flow phenomenon of milk which may occur during milking by milker. The duration of pasteurizative effect is relatively short (for example, 1–2 hours after dipping), and such effect disappears up to next milking, with pasteurization after milking i.e. post-dipping alone, and therefore, the effect for environmental mastitis-causing bacterium is limited.

As described above, in said post-dipping treatment, there are problems that it is unable to expect effect against infection from pre-existing bacterium and that effect against the environmental mastitis is also limited. Technology proposed in order to overcome such prior problems is a treatment for pasteurizing or sterilizing teats before milking (pre-dipping method). It was reported by Nakagawa, Furukawa and Nakajima that *Staphylococcus aureus* and *Streptococcus* were significantly less inhabited and milk quality was maintained more healthily in a farm in which pre-dipping was carried out, compared to one in which washing by towel was carried out, and thus pre-dipping treatment was thought to be effective.

As such, there is a literature disclosed that the dip pasteurization of teats before milking (hereafter, refers to pre-dipping) is effective for prevention from mastitis. However, since the pre-dipping is a treatment before milking, certain problem occurs that when the post-dipping agent is used as pre-dipping agent, it has high viscosity, iodine contained therein adheres to teats for any length of time, whereby iodine migrates into milk and retains in milk stocks. Therefore, it was shown that such agent adhered to teats after pre-dipping needs to be sufficiently removed.

Accordingly, there are needed a development of low or less iodine containing products which have low after-effectiveness (viscosity). The post-dipping agent and pre-dipping agent should be products which meet the respective demand, respectively. However, there is yet obtained no suitable product which can be employed as pre-dipping agent in Japan.

Therefore, since development of mastitis is a serious problem for dairy farmers, it may be thought that there are problems such as use of the post-dipping agent as pre-dipping, use of the post-dipping agent departing from the indication of animal medicine, migration of iodine into milk and the like. In order to settle these problems, appearance of disinfectant for teats which can be effectively as pre-dipping agent, is desired.

The following bacteria of the genus *Brachybacterium* are currently known.

*Brachybacterium conglomeratum*

*Brachybacterium faecium*

*Brachybacterium nesterenkovii*

*Brachybacterium paraconglomeratum*

*Brachybacterium rhamnosum*

However, absolutely no investigation has been done about the industrial applicability of these bacteria of the genus *Brachybacterium*.

Therefore, the inventors of the present invention made investigations about the genus *Brachybacterium*. As a result, it has been found that *Brachybacterium* species have an anti-microbial activity against *Staphylococcus aureus* of mastitis-causing bacteria.

Based on this finding, it is an object of the invention to provide a method for a disinfectant for teats of animals, and a method for improving microorganism-environment harmful for animals including the said *Brachybacterium* species.

DISCLOSURE OF INVENTION

The disinfectant for teats of animals of this invention is characterized in that it comprises a microorganism belonging to the genus *Brachybacterium*.

The said microorganism belonging to the genus *Brachybacterium* is preferable to use a novel microorganism having the following bacteriological properties.

| | |
|---|---|
| 1. Morphology: | Polymorphic bacillus |
| 2. Gram staining: | + |
| 3. Spore: | – |
| 4. Mobility: | – |
| 5. Oxygen behavior: | Aerobic |
| 6. Oxidase: | – |
| 7. Catalase: | + |
| 8. Color of colony: | Yellowish |
| 9. Acid fastness: | – |
| 10. Rod-coccus cycle: | + |
| 11. Elongation of peripheral cells around colony: | – |

-continued

| | |
|---|---|
| 12. Diamino acid in cell wall: | Meso-diaminopimelic acid |
| 13. Glycolyl test: | − (Acetyl type) |
| 14. Arabinogalactan polymer in cell wall: | − |
| 15. Mycolic acid: | − |
| 16. Quinone series: | MK-7, MK-8 |
| 17. GC content in bacterial DNA: | 72 mol % |
| 18. Reduction of nitrate: | + |
| 19. Denitrogen reaction: | + |
| 20. Methyl red test: | − |
| 21. V-P Reaction: | − |
| 22. Indole generation: | − |
| 23. Hydrogen sulfide generation: | |
| In TSI agar: | − |
| In lead acetate agar: | − |
| 24. Starch hydrolysis: | + |
| 25. Utilization of citrate: | |
| In Koser's culture medium: | − |
| In Christensen's culture medium: | − |
| 26. Utilization of inorganic nitrogen source: | |
| For nitrate salt | − |
| For ammonium salt | Slight |
| 27. Formation of dye | + (Yellowish) |
| 28. Urease | − |
| 29. Oxidase | − |
| 30. Range of growth: | |
| pH | From 6.0 to 10.0 |
| Temperature | From 9 to 42° C. |
| 31. Formation of acid: | |
| D-Arabinose: | − |
| L-Arabinose: | + |
| D-Xylose: | + |
| D-Glucose: | + |
| D-Mannose: | + |
| D-Fructose: | + |
| D-Galactose: | + |
| Maltose: | + |
| Sucrose: | + |
| Lactose: | + |
| Trehalose: | + |
| D-Sorbitol: | − |
| D-Mannitol: | + |
| Inositol: | − |
| Glycerin: | + |
| Starch: | + |
| Melezitose: | − |
| D-Ribose: | − |
| 32. Formation of gas: | |
| L-Arabinose: | − |
| D-Xylose: | − |
| D-Glucose: | − |
| D-Mannose: | − |
| D-Fructose: | − |
| D-Galactose: | − |
| Maltose: | − |
| Sucrose: | − |
| Lactose: | − |
| Trehalose: | − |
| D-Sorbitol: | − |
| D-Mannitol: | − |
| Inositol: | − |
| Glycerin: | − |
| Starch: | − |

In addition, a method for improving microorganism-environment harmful for animals of the invention is characterized in that it comprises spraying a microorganism belonging to the genus *Brachybacterium* in surroundings where animals live.

Further, a method for improving microorganism-environment harmful for animals of the invention is characterized in that it comprises immobilizing a microorganism belonging to the genus *Brachybacterium* to a veil for covering an animal, formed by a cloth or paper and coating the animal by the said veil.

Furthermore, a method for improving microorganism-environment harmful for animals of the invention is characterized in that it comprises immobilizing a microorganism belonging to the genus *Brachybacterium* to a cloth or paper, and placing the cloth or paper in surroundings where animals live.

The microorganism belonging to the genus *Brachybacterium* using for the said methods for improving microorganism-environment harmful for animals is preferably the novel microorganism in the genus *Brachybacterium* mentioned above.

BEST MODE FOR CARRYING OUT THE INVENTION

Figure 1:
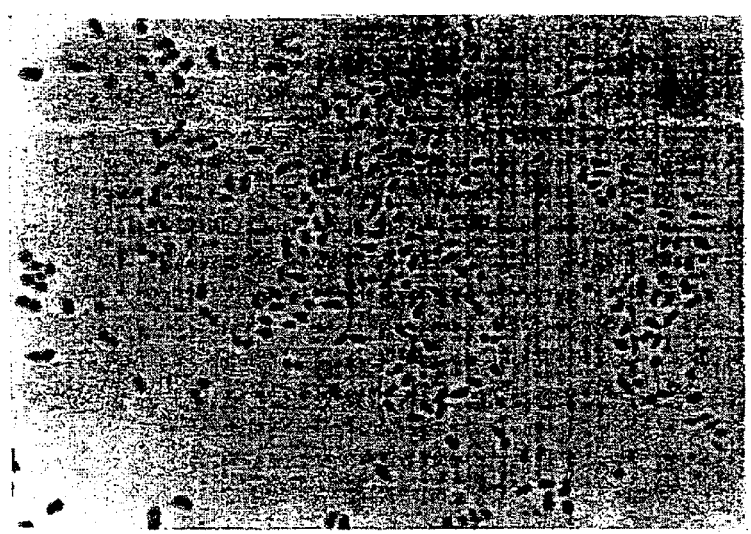
FIG. 1 is a figure representing a microscopic photograph of the morphology of a novel microorganism of the invention.

The disinfectant for teats of the invention includes a microorganism belonging to the genus *Brachybacterium*.

As the microorganism belonging to the genus *Brachybacterium*, the following microorganisms belonging to the novel genus *Brachybacterium* can be used, apart from the above-mentioned well-known *Brachybacterium conglomeratum Brachybacterium faecium, Brachybacterium nesterenkovii, Brachybacterium paraconglomeratum, Brachybacterium rhamnosum*.

The tests of the bacteriological properties of the novel *Brachybacterium* species and their classification were carried out according to the descriptions of the following references.

(1) *International Journal Systematic Bacteriology*, Vol. 38, pp. 45–48 (1988).
(2) *International Journal Systematic Bacteriology*, Vol. 42, pp. 74–78 (1992).
(3) *International Journal Systematic Bacteriology*, Vol. 46, pp. 81–87 (1996).
(4) *International Journal Systematic Bacteriology*, Vol. 45, pp. 160–168 (1995).

Consequently, the microorganism is identified as a *Brachybacterium* species because the microorganism is a Gram-positive *bacillus* showing a polymorph with no spore; but the results of the analysis of the bacterial components did not agree with any of the bacterial species described in the references. Thus, the microorganism is confirmed as a novel bacterium belonging to the genus *Brachybacterium*. The bacterium is deposited as a bacterial strain AAA-a of the genus *Brachybacterium* (Accession No. FERM BP-6848) deposited in the International Depositary Authority for the deposit of microorganism.

The bacterial properties of the novel microorganism belonging to the genus *Brachybacterium* are described below.

| | |
|---|---|
| 1. Morphology: | Polymorphic bacillus (see FIGS. 1 and 2) |
| 2. Gram staining: | + |
| 3. Spore: | − |
| 4. Mobility: | − |
| 5. Oxygen behavior: | Aerobic |
| 6. Oxidase: | − |
| 7. Catalase: | + |
| 8. Color of colony: | Yellowish |
| 9. Acid fastness: | − |
| 10. Rod-coccus cycle: | + (See FIGS. 1 and 2) |
| 11. Elongation of peripheral cells around colony: | − |
| 12. Diamino acid in cell wall: | Meso-diaminopimelic acid (estimated on the basis of acid hydrolysates from all cells) |
| 13. Glycolyl test: | − (Acetyl type) |
| 14. Arabinogalactan polymer in cell wall: | − (Estimated on the basis of acid hydrolysates from all cells) |
| 15. Mycolic acid: | − |
| 16. Quinone series: | MK-7, MK-8 |
| 17. GC content in bacterial DNA (determined by HPLC): | 72 mol % |
| 18. Reduction of nitrate: | + |
| 19. Denitrogen reaction: | + |
| 20. Methyl red test: | − |
| 21. V-P Reaction: | − |
| 22. Indole generation: | − |
| 23. Hydrogen sulfide generation: | |
| In TSI agar: | − |
| In lead acetate agar: | − (Lead acetate test paper was suspended for the test, with no addition of lead acetate) |
| 24. Starch hydrolysis: | + |
| 25. Utilization of citrate: | |
| In Koser's culture medium: | − |
| In Christensen's culture medium: | − |
| 26. Utilization of inorganic nitrogen source: | |
| For nitrate salt: | − |
| For ammonium salt: | Slight |
| 27. Formation of dye: | + (Yellowish) |
| 28. Urease: | − |
| 29. Oxidase: | − |
| 30. Range of growth (bouillon broth was used for test): | |
| pH (at an interval of 0.5): | From 6.0 to 10.0 |
| Temperature (at an interval of 1° C.): | From 9 to 42° C. |
| 31. Formation of acid: | |
| D-Arabinose: | − |
| L-Arabinose: | + |
| D-Xylose: | + |
| D-Glucose: | + |
| D-Mannose: | + |
| D-Fructose: | + |
| D-Galactose: | + |
| Maltose: | + |
| Sucrose: | + |
| Lactose: | + |
| Trehalose: | + |
| D-Sorbitol: | − |
| D-Mannitol: | + |
| Inositol: | − |
| Glycerin: | + |
| Starch: | + |
| Melezitose: | − |
| D-Ribose: | − |

-continued

| | |
|---|---|
| 32. Formation of gas: | |
| L-Arabinose: | − |
| D-Xylose: | − |
| D-Glucose: | − |
| D-Mannose: | − |
| D-Fructose: | − |
| D-Galactose: | − |
| Maltose: | − |
| Sucrose: | − |
| Lactose: | − |
| Trehalose: | − |
| D-Sorbitol: | − |
| D-Mannitol: | − |
| Inositol: | − |
| Glycerin: | − |
| Starch: | − |

This novel microorganism of the invention can grow well in any of general nutrient culture media.

The microorganism is cultured preferably at about 5 to 30° C., and most preferably at about 18 to 27° C., so that the microorganism grows very well.

The morphological properties of the novel microorganism of the invention are as follows.

(1) Cell Morphology and Size 1-1. Culturing in Bouillon Agar Culture Medium

Short *bacillus,* polymorphic, of a size of 1.2 to 1.4×1.5 to 1.9 microns, when the bacterium is cultured at 30° C. for 6 hours; and

*Coccobacillus* of a size of 1.2 to 1.4×1.2 to 1.5 microns, when the bacterium is cultured at 30° C. for 24 hours.

1-2. Culturing in Bouillon Liquid Culture Medium

*Coccobacillus* of a size of 1.0 to 1.2×1.3 to 1.4 microns, when the bacterium is cultured at 30° C. for 24 hours.

(2) Polymorphic Cell Property

Figure 2:
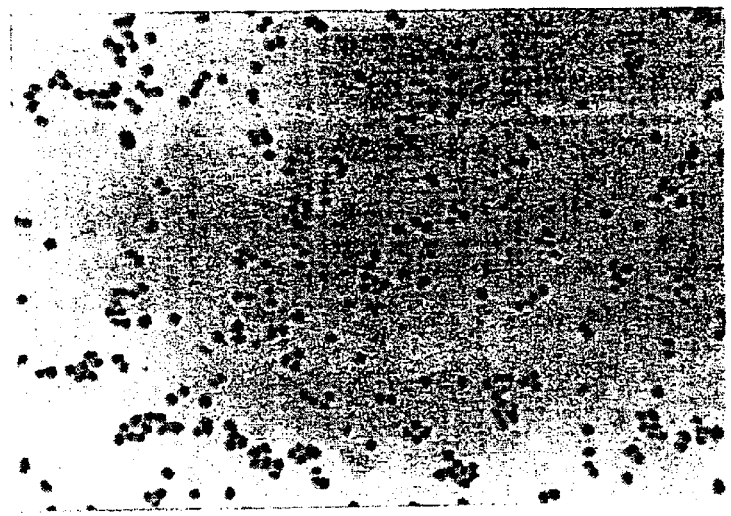
FIG. 2 is a figure representing a microscopic photograph of the morphology of a novel microorganism of the invention.

Polymorphic property with rod-coccus cycle under observation (see FIGS. 1 and 2).

(3) No Mobility Found (4) No Spore Formation Observed

The properties of the novel microorganism according to the invention under culture in individual culture media are as follows.

(1) Culturing in Bouillon Agar Plate Culture Medium

Smooth and glossy colonies with periphery under observation.

Yellowish colony dyes generated under observation.

(2) Culturing in Bouillon Liquid Culture Medium

Growing bacteria with precipitates in the overall culture medium under observation.

No surface film generated under observation.

(3) Culturing by Using Bouillon Gelatin Puncture

Bacterial growth in the upper culture medium, but no liquefaction observed.

(4) Culturing in Litmus Milk

Growing bacteria observed in the overall culture medium, with no solidification or liquefaction observed.

Growing acid slightly observed.

The novel bacterium belonging to the genus *Brachybacterium* can be cultured in bouillon culture medium or the like and the culture solution per se can be used as a disinfectant for teats of the invention. In addition, this solution is diluted with aqua pura or physiological salt solution, or is condensed, whereby it can be used accretive a moisture retention such as glycerin or the like. Moreover, the said culture solution is centrifuged, and then only a bacterial body was abstracted and dried, whereby a resulting powder can be used also as a powdery disinfectant for teats.

The said disinfectant for teats of animals can be applied to teats of animals by dipping (both pre-dipping and post-dipping are effective), spraying or coating.

The said disinfectant for teats in this invention has antibacterial function against *Staphylococcus aureus*, and also can be as indigenous bacteria and prevent other bacteria from living there. As mentioned above, the said disinfectant for teats of this invention affects as a preventive agent on teats of cows and the like.

The said microorganism belonging to the genus *Brachybacterium* can be used for improving microorganism-environment of a livestock barn such as a cow barn and the like.

In this case, a microorganism group belonging to the genus *Brachybacterium* is immobilized on a carrier and used as the carrier-immobilized microorganism group for easy handling.

As the carrier immobilizing microorganism group, larger retention volume of the microorganism and readily promoting activation of the microorganism are preferable.

As the carrier, preferably, use is made of rocks (for example, pearlite and diatomaceous earth) or ground rocks, pebble, sand, plastics, ceramics (for example, alumina, silica, natural zeolite, and synthetic zeolite), or talc; specifically, use is preferably made of porous materials with continuous air pores, such as porous ceramics and porous plastics. Preference is given for example to a microfine powder (Pearlite as a trade name) capable of exerting a property to grow bacteria, which is prepared by keeping ground pearlite at a high temperature and a high pressure to thermally treat the pearlite and subsequently reducing the pressure rapidly. Preferably, the pore size of such porous materials is about 2 to 10 $\mu$m. The form of such carrier (form) is any of mass, granule, powder, fine powder, plate material or needle-like material, but preferably, the form is a powdery granule of an average particle size of 2 mm or less, and particularly about 50 $\mu$m to 1 mm. If necessary, such carrier-immobilized microorganism group may satisfactorily be placed in a container with good water permeability or air permeability, including cloths or nets.

As the carrier, use may be made of a woven fabric, non-woven fabric or paper in the form of ribbon or sheet, satisfactorily.

In order to immobilize the microorganism to such carrier, the carrier and a dispersion liquid of the microorganism group are mixed and then it is dried. However, the carrier per se also may be cultured the microorganism group directly.

The amount of the microorganism group immobilized on the carrier differs, depending on the conditions for immobilization, but the amount is preferably from 5 cells to 200 hundred million cells/cm$^3$, and more preferably from 10 bodies to 100 hundred million cells/cm$^3$.

As the carrier, use may be made of porous materials, it can be disseminated as it is on a floor or included in coating materials such as a wall or pillar. On the other hands, as the carrier, use may be made of a woven fabric, non-woven fabric or paper in the form of ribbon or sheet, it can be used as a veil for covering an animal's back or the like.

Furthermore, the said fabric or paper is placed in surroundings where animals live, for example, hanging it a wall in a barn, or lining it with a floor, whereby the microorganism belonging to the genus *Brachybacterium* becomes indigenous bacteria, and restrains other bacteria from breeding. Therefore, microorgaism-environment of animals in surroundings where animals live can be improved.

As described above, when the microorganism belonging to the genus *Brachybacterium* is used in surroundings where animals live, it is effective to degerm disease-causing bacteria of *Staphylococcus aureus* or the like, whereby the microorgaism-environment can be improved. In addition, the deodorizing effect has been confirmed in a cow barn and the like.

The safety of the said *Brachybacterium* AAA-a has confirmed by the following acute toxicity test and skin irritation study using laboratory mice.

Acute Toxicity Test

1. Out line of the test: A *Brachybacterium* AAA-a was cultured in a bouillon liquid culture medium and an acute toxicity test was conducted to laboratory mice using a culture solution containing a bacterial body thereof.

2. Test Method
   (1) Bacterial strain: *Brachybacterium* AAA-a
   (2) Adjusted bacterial solution: A *Brachybacterium* AAA-a was inoculated in a bouillon liquid culture medium (Bacto-peptone 1%, Beef extract 0.5%, Sodium chloride 5%) for agitation culture at 30° C. for 18 hours, and then culture solution (approximately 10$^9$/ml cells) was obtained as a "bacterial solution".
   Moreover, as a "clear supernatant liquid", the culture solution was centrifuged (10,000 rpm, 15 min) and eliminated the bacterial body.
   (3) Test operation: Breeding laboratory mice (Hr/Kud.the fifth weeks) were divided into the following three groups by three mice of each sex and were bred in each cage. Then each weight was measured per week. Surroundings of breeding: Room temperature: 25° C., Humidity: approximately 50%, Feed: free<amount of water: 4 to 6 g/day/mouse, amount of feed: 4 to 6 g/day/mouse>
   1-1.Control: Water (tap water)
      Food (commercial pellet formula food*)
      *Pellet foods of corn: 30%, fish flour: 5%, bean cake: 12%, flour: 35%, wheat bran: 8%, alfalfa: 3%, yeast: 3%, salt: 0.5%, mixed vitamin: 1.8%, mixed mineral: 0.2% and calcium carbonate: 1.5% (total: 100%).
   1-2.Clear supernatant liquid:
      Water (tap water)+10% added "clear supernatant liquid"
      Food (commercial pellet formula food)
   1-3.Bacterial solution: water (tap water)+10% impregnated/dried "bacterial solution"
3. Test result: As shown in Table-1, remarkable differences on growth and figure of mice in any of the control from 1-1 to 1-3 were not confirmed.
   In other words, it is believed that there is no acute toxicity in the bacterial body and culture solution of *Brachybacterium* AAA-a, as no affect was found for 5 weeks to the growth of mice in this test.

TABLE 1

Acute toxicity test against mice of Brachybacterium AAA-a
<Evaluation test against growth>

| Test location Duration of breeding | Sex | ① Control Weight (g) | Average (g) | ② Clear supernatant liquid Weight (g) | Average (g) | ③ Bacterial solution Weight (g) | Average (g) |
|---|---|---|---|---|---|---|---|
| The 5th week | ♂ | 19.4 | 20.1 | 19.3 | 20.0 | 19.5 | 20.2 |
|  |  | 20.1 |  | 19.9 |  | 20.2 |  |
|  |  | 20.8 |  | 20.9 |  | 20.8 |  |
|  | ♀ | 17.7 | 18.9 | 17.8 | 19.0 | 17.7 | 18.9 |
|  |  | 18.9 |  | 19.0 |  | 18.8 |  |
|  |  | 20.0 |  | 20.1 |  | 20.2 |  |
| The 6th week | ♂ | 23.5 | 24.7 | 23.9 | 24.7 | 24.1 | 25.0 |
|  |  | 24.7 |  | 24.5 |  | 25.1 |  |
|  |  | 25.9 |  | 25.8 |  | 25.7 |  |
|  | ♀ | 21.1 | 22.8 | 21.2 | 22.9 | 21.1 | 22.9 |
|  |  | 22.9 |  | 23.0 |  | 22.8 |  |
|  |  | 24.5 |  | 24.6 |  | 24.7 |  |
| The 7th week | ♂ | 26.5 | 28.2 | 26.9 | 28.5 | 27.1 | 28.5 |
|  |  | 28.2 |  | 28.6 |  | 28.6 |  |
|  |  | 30.0 |  | 29.9 |  | 29.8 |  |
|  | ♀ | 24.0 | 25.8 | 24.3 | 25.9 | 24.1 | 25.8 |
|  |  | 25.8 |  | 26.0 |  | 25.8 |  |
|  |  | 27.6 |  | 27.5 |  | 27.6 |  |
| The 8th week | ♂ | 27.1 | 29.0 | 27.9 | 29.3 | 28.0 | 29.3 |
|  |  | 29.0 |  | 29.4 |  | 29.4 |  |
|  |  | 31.0 |  | 30.5 |  | 30.4 |  |
|  | ♀ | 24.4 | 26.2 | 24.8 | 26.4 | 24.6 | 26.3 |
|  |  | 26.2 |  | 26.4 |  | 26.3 |  |
|  |  | 28.1 |  | 27.9 |  | 28.1 |  |
| The 9th week | ♂ | 27.9 | 29.9 | 28.9 | 30.2 | 29.0 | 30.3 |
|  |  | 29.9 |  | 30.3 |  | 30.4 |  |
|  |  | 32.0 |  | 31.3 |  | 31.4 |  |
|  | ♀ | 25.3 | 27.2 | 25.9 | 27.4 | 25.7 | 27.3 |
|  |  | 27.3 |  | 27.4 |  | 27.3 |  |
|  |  | 29.0 |  | 28.8 |  | 29.0 |  |
| The 10th week | ♂ | 29.4 | 31.1 | 30.4 | 31.4 | 30.5 | 31.5 |
|  |  | 31.0 |  | 31.5 |  | 31.7 |  |
|  |  | 33.0 |  | 32.3 |  | 32.4 |  |
|  | ♀ | 25.8 | 27.7 | 26.5 | 27.8 | 26.2 | 27.8 |
|  |  | 27.7 |  | 27.8 |  | 27.7 |  |
|  |  | 29.6 |  | 29.2 |  | 29.4 |  |

Skin Irritation Study

1. Out line of the test: A *Brachybacterium* AAA-a was cultured in a bouillon liquid culture medium and a skin irritation study was conducted to laboratory mice using a culture solution containing a bacterial body thereof.
2. Test method:
(1) Bacterial strain: *Brachybacterium* AAA-a
(2) Adjusted bacterial solution: A *Brachybacterium* AAA-a was inoculated in a bouillon liquid culture medium (Bacto-peptone 1%, Beef extract 0.5%, Sodium chloride 0.5%) for agitation culture at 30° C. for 18 hours, and then the a culture solution (approximately $10^9$/ml cells) was obtained as a "bacterial solutions".
(3) Test operation: Breeding laboratory mice (Hr/Kud.the fifth weeks) were divided into the following two groups by three mice of each sex, and were bred in each cage. Then irritation to the skin of mice applying (For a control, water is applied with the same operation.) the "bacterial solution" on the right and left side of the back for each mouse by 100 μm was observed once a day for 2 weeks.

Surroundings of breeding: Room temperature: 25° C., Humidity: approximately 50%, Feed: free<amount of water: 4 to 6 g/day/mouse, amount of feed: 4 to 6 g/day/mouse>
1-1. Control: ♂<three mice: A~C>♀<three mice: D~F>
Water (tap water)
Food (commercial pellet formula food*)
1-2. Bacterial solution: ♂<three mice: a~c>♀<three mice: d~f>
Water (tap water)
Food (commercial pellet formula food*)+10% impregnated/dried "bacterial solution"
3. Test result: As shown in Table-2, abnormality of skin on back, nose and around mouth for each mouse in any of the controls 1-1 and 1-2 were not confirmed.

In other words, it is believed that there is no skin irritation in the bacterial body and culture solution of *Brachybacterium* AAA-a, as no affect was found for 2 weeks to the skin of mice in this test.

TABLE 2

Skin irritation study against mice of Brachybacterium AAA-a

| | | \multicolumn{14}{c}{Number of days} |
|---|---|---|---|---|---|---|---|---|---|---|---|---|---|---|---|
| | | 1 | 2 | 3 | 4 | 5 | 6 | 7 | 8 | 9 | 10 | 11 | 12 | 13 | 14 |
| ① Control location | | | | | | | | | | | | | | | |
| ♂ Back | A | - | - | - | - | - | - | - | - | - | - | - | - | - | - |
| | B | - | - | - | - | - | - | - | - | - | - | - | - | - | - |
| | C | - | - | - | - | - | - | - | - | - | - | - | - | - | - |
| ♂ Nose/Mouth | A | - | - | - | - | - | - | - | - | - | - | - | - | - | - |
| | B | - | - | - | - | - | - | - | - | - | - | - | - | - | - |
| | C | - | - | - | - | - | - | - | - | - | - | - | - | - | - |
| ♀ Back | D | - | - | - | - | - | - | - | - | - | - | - | - | - | - |
| | E | - | - | - | - | - | - | - | - | - | - | - | - | - | - |
| | F | - | - | - | - | - | - | - | - | - | - | - | - | - | - |
| ♀ Nose/Mouth | D | - | - | - | - | - | - | - | - | - | - | - | - | - | - |
| | E | - | - | - | - | - | - | - | - | - | - | - | - | - | - |
| | F | - | - | - | - | - | - | - | - | - | - | - | - | - | - |
| ② Bacterial solution | | | | | | | | | | | | | | | |
| ♂ Back | a | - | - | - | - | - | - | - | - | - | - | - | - | - | - |
| | b | - | - | - | - | - | - | - | - | - | - | - | - | - | - |
| | c | - | - | - | - | - | - | - | - | - | - | - | - | - | - |
| ♂ Nose/Mouth | a | - | - | - | - | - | - | - | - | - | - | - | - | - | - |
| | b | - | - | - | - | - | - | - | - | - | - | - | - | - | - |
| | c | - | - | - | - | - | - | - | - | - | - | - | - | - | - |
| ♀ Back | d | - | - | - | - | - | - | - | - | - | - | - | - | - | - |
| | e | - | - | - | - | - | - | - | - | - | - | - | - | - | - |
| | f | - | - | - | - | - | - | - | - | - | - | - | - | - | - |
| ♀ Nose/Mouth | d | - | - | - | - | - | - | - | - | - | - | - | - | - | - |
| | e | - | - | - | - | - | - | - | - | - | - | - | - | - | - |
| | f | - | - | - | - | - | - | - | - | - | - | - | - | - | - |

++: Strong irritation
+: Irritation
-: No irritation

EXAMPLES

The invention is now described in detail with reference to the following Examples.

Example 1

First of all, a culture medium of the following composition was prepared.
Culture Medium
 Peptone 5 g
 Meat extract 5 g
 Water 500 ml
 pH of culture medium 6.8±0.2

A bacterial strain of the genus *Brachybacterium* AAA-a was inoculated in the culture medium of the above composition, for agitation culture at 30° C. When the bacteria reached a logarithmic phase, the culture solution was diluted with a sterilized aqua pura to adjust the viable cell number $1 \times 10^8$/ml; and the adjusted solution was used as a post-dipping solution for pre-dipping at teats of cows by the conventional method, the bacterial number of *Staphylococcus aureus* on the surface of skin of teats was decreased. The same experiment was done on other *Brachybacterium* species other than the aforementioned species. The similar effect was obtained, although the function was poorer than that observed in the case of the novel bacterial strain.

Moreover, the said culture solution was diluted 100 times with aqua pura, to adhere to a carrier, and was dried to prepare a powder. As the carrier, use was made of burned and ground diatomaceous earth.

This powdery bacterial strain of *Brachybacterium* AAA-a was sprayed about 50 g per 1 square m in a barn of cows. At this time, total number of bacteria per gram in the powder was around $10^5$ cells. In this circumstance, after 24 hours passed, when the bacterial number of *Staphylococcus aureus* was measured, it was clearly decreased. Besides, deodorant effect was confirmed.

As described above, the effect of this invention was clear.

What is claimed is:

1. A disinfectant for teats of animals of this invention is characterized in that it comprises a microorganism belonging to genus *Brachybacterium*.

2. The disinfectant for teats of animals according to claim 1, wherein the said novel microorganism of the genus *Brachybacterium* has the following bacteriological properties:

| | |
|---|---|
| 1. Morphology: | Polymorphic bacillus |
| 2. Gram staining: | + |
| 3. Spore: | - |
| 4. Mobility: | - |
| 5. Oxygen behavior: | Aerobic |
| 6. Oxidase: | - |
| 7. Catalase: | + |
| 8. Color of colony: | Yellowish |
| 9. Acid fastness: | - |
| 10. Rod-coccus cycle: | + |
| 11. Elongation of peripheral cells around colony: | - |
| 12. Diamino acid in cell wall: | Meso-diaminopimelic acid |
| 13. Glycolyl test: | - (Acetyl type) |
| 14. Arabinogalactan polymer in cell wall: | - |
| 15. Mycolic acid: | - |
| 16. Quinone series: | MK-7, MK-8 |
| 17. GC content in bacterial DNA: | 72 mol % |
| 18. Reduction of nitrate: | + |

-continued

| | |
|---|---|
| 19. Denitrogen reaction: | + |
| 20. Methyl red test: | − |
| 21. V-P Reaction: | − |
| 22. Indole generation: | − |
| 23. Hydrogen sulfide generation: | |
|     In TSI agar: | − |
|     In lead acetate agar: | − |
| 24. Starch hydrolysis: | + |
| 25. Utilization of citrate: | |
|     In Koser's culture medium: | − |
|     In Christensen's culture medium: | − |
| 26. Utilization of inorganic nitrogen source: | |
|     For nitrate salt: | − |
|     For ammonium salt: | Slight |
| 27. Formation of dye: | + (Yellowish) |
| 28. Urease: | − |
| 29. Oxidase: | − |
| 30. Range of growth: | |
|     pH: | From 6.0 to 10.0 |
|     Temperature: | From 9 to 42° C. |
| 31. Formation of acid: | |
|     D-Arabinose: | − |
|     L-Arabinose: | + |
|     D-Xylose: | + |
|     D-Glucose: | + |
|     D-Mannose: | + |
|     D-Fructose: | + |
|     D-Galactose: | + |
|     Maltose: | + |
|     Sucrose: | + |
|     Lactose: | + |
|     Trehalose: | + |
|     D-Sorbitol: | − |
|     D-Mannitol: | + |
|     Inositol: | − |
|     Glycerin: | + |
|     Starch: | + |
|     Melezitose: | − |
|     D-Ribose: | − |
| 32. Formation of gas: | |
|     L-Arabinose: | − |
|     D-Xylose: | − |
|     D-Glucose: | − |
|     D-Mannose: | − |
|     D-Fructose: | − |
|     D-Galactose: | − |
|     Maltose: | − |
|     Sucrose: | − |
|     Lactose: | − |
|     Trehalose: | − |
|     D-Sorbitol: | − |
|     D-Mannitol: | − |
|     Inositol: | − |
|     Glycerin: | − |
|     Starch: | −. |

3. A method for improving microorganism-environment harmful for animals is characterized it comprises spraying a microorganism belonging to the genus *Brachybacterium* in surroundings where animals live.

4. The method for improving microorganism-environment harmful for animals according to claim 3, wherein the said novel microorganism of the genus *Brachybacterium* has the following bacteriological properties:

| | |
|---|---|
| 1. Morphology: | Polymorphic bacillus |
| 2. Gram staining: | + |

-continued

| | |
|---|---|
| 3. Spore: | − |
| 4. Mobility: | − |
| 5. Oxygen behavior: | Aerobic |
| 6. Oxidase: | − |
| 7. Catalase: | + |
| 8. Color of colony: | Yellowish |
| 9. Acid fastness: | − |
| 10. Rod-coccus cycle: | + |
| 11. Elongation of peripheral cells around colony: | − |
| 12. Diamino acid in cell wall: | Meso-diaminopimelic acid |
| 13. Glycolyl test: | − (Acetyl type) |
| 14. Arabinogalactan polymer in cell wall: | − |
| 15. Mycolic acid: | − |
| 16. Quinone series: | MK-7, MK-8 |
| 17. GC content in bacterial DNA: | 72 mol % |
| 18. Reduction of nitrate: | + |
| 19. Denitrogen reaction: | + |
| 20. Methyl red test: | − |
| 21. V-P Reaction: | − |
| 22. Indole generation: | − |
| 23. Hydrogen sulfide generation: | |
|     In TSI agar: | − |
|     In lead acetate agar: | − |
| 24. Starch hydrolysis: | + |
| 25. Utilization of citrate: | |
|     In Koser's culture medium: | − |
|     In Christensen's culture medium: | − |
| 26. Utilization of inorganic nitrogen source: | |
|     For nitrate salt: | − |
|     For ammonium salt: | Slight |
| 27. Formation of dye: | + (Yellowish) |
| 28. Urease: | − |
| 29. Oxidase: | − |
| 30. Range of growth: | |
|     pH: | From 6.0 to 10.0 |
|     Temperature: | From 9 to 42° C. |
| 31. Formation of acid: | |
|     D-Arabinose: | − |
|     L-Arabinose: | + |
|     D-Xylose: | + |
|     D-Glucose: | + |
|     D-Mannose: | + |
|     D-Fructose: | + |
|     D-Galactose: | + |
|     Maltose: | + |
|     Sucrose: | + |
|     Lactose: | + |
|     Trehalose: | + |
|     D-Sorbitol: | − |
|     D-Mannitol: | + |
|     Inositol: | − |
|     Glycerin: | + |
|     Starch: | + |
|     Melezitose: | − |
|     D-Ribose: | − |
| 32. Formation of gas: | |
|     L-Arabinose: | − |
|     D-Xylose: | − |
|     D-Glucose: | − |
|     D-Mannose: | − |
|     D-Fructose: | − |
|     D-Galactose: | − |
|     Maltose: | − |
|     Sucrose: | − |
|     Lactose: | − |
|     Trehalose: | − |
|     D-Sorbitol: | − |
|     D-Mannitol: | − |
|     Inositol: | − |
|     Glycerin: | − |
|     Starch: | −. |

5. A method for improving microorganism-environment harmful for animals is characterized in that it comprises immobilizing a microorganism belonging to the genus *Brachybacterium* to a veil for covering an animal, formed by a cloth or paper and coating the animal by the said veil.

6. The method for improving microorganism-environment harmful for animals according to claim 5, wherein the said novel microorganism of the genus *Brachybacterium* has the following bacteriological properties:

| | | |
|---|---|---|
| 1. | Morphology: | Polymorphic bacillus |
| 2. | Gram staining: | + |
| 3. | Spore: | − |
| 4. | Mobility: | − |
| 5. | Oxygen behavior: | Aerobic |
| 6. | Oxidase: | − |
| 7. | Catalase: | + |
| 8. | Color of colony: | Yellowish |
| 9. | Acid fastness: | − |
| 10. | Rod-coccus cycle: | + |
| 11. | Elongation of peripheral cells around colony: | − |
| 12. | Diamino acid in cell wall: | Meso-diaminopimelic acid |
| 13. | Glycolyl test: | − (Acetyl type) |
| 14. | Arabinogalactan polymer in cell wall: | − |
| 15. | Mycolic acid: | − |
| 16. | Quinone series: | MK-7, MK-8 |
| 17. | GC content in bacterial DNA (determined by HPLC): | 72 mol % |
| 18. | Reduction of nitrate: | + |
| 19. | Denitrogen reaction: | + |
| 20. | Methyl red test: | − |
| 21. | V-P Reaction: | − |
| 22. | Indole generation: | − |
| 23. | Hydrogen sulfide generation: | |
| | In TSI agar: | − |
| | In lead acetate agar: | − |
| 24. | Starch hydrolysis: | + |
| 25. | Utilization of citrate: | |
| | In Koser's culture medium: | − |
| | In Christensen's culture medium: | − |
| 26. | Utilization of inorganic nitrogen source: | |
| | For nitrate salt: | − |
| | For ammonium salt: | Slight |
| 27. | Formation of dye: | + (Yellowish) |
| 28. | Urease: | − |
| 29. | Oxidase: | − |
| 30. | Range of growth: | |
| | pH: | From 6.0 to 10.0 |
| | Temperature: | From 9 to 42° C. |
| 31. | Formation of acid: | |
| | D-Arabinose: | − |
| | L-Arabinose: | + |
| | D-Xylose: | + |
| | D-Glucose: | + |
| | D-Mannose: | + |
| | D-Fructose: | + |
| | D-Galactose: | + |
| | Maltose: | + |
| | Sucrose: | + |
| | Lactose: | + |
| | Trehalose: | + |
| | D-Sorbitol: | − |
| | D-Mannitol: | + |
| | Inositol: | − |
| | Glycerin: | + |
| | Starch: | + |
| | Melezitose: | − |
| | D-Ribose: | − |

-continued

| | | |
|---|---|---|
| 32. | Formation of gas: | |
| | L-Arabinose: | − |
| | D-Xylose: | − |
| | D-Glucose: | − |
| | D-Mannose: | − |
| | D-Fructose: | − |
| | D-Galactose: | − |
| | Maltose: | − |
| | Sucrose: | − |
| | Lactose: | − |
| | Trehalose: | − |
| | D-Sorbitol: | − |
| | D-Mannitol: | − |
| | Inositol: | − |
| | Glycerin: | − |
| | Starch: | −. |

7. A method for improving microorganism-environment harmful for animals is characterized in that it comprises immobilizing a microorganism belonging to the genus *Brachybacterium* to a cloth or paper, and placing the cloth or paper in surroundings where animals live.

8. The method for improving microorganism-environment harmful for animals according to claim 7, wherein the said novel microorganism of the genus *Brachybacterium* has the following bacteriological properties:

| | | |
|---|---|---|
| 1. | Morphology: | Polymorphic bacillus |
| 2. | Gram staining: | + |
| 3. | Spore: | − |
| 4. | Mobility: | − |
| 5. | Oxygen behavior: | Aerobic |
| 6. | Oxidase: | − |
| 7. | Catalase: | + |
| 8. | Color of colony: | Yellowish |
| 9. | Acid fastness: | − |
| 10. | Rod-coccus cycle: | + |
| 11. | Elongation of peripheral cells around colony: | − |
| 12. | Diamino acid in cell wall: | Meso-diaminopimelic acid |
| 13. | Glycolyl test: | (Acetyl type) |
| 14. | Arabinogalactan polymer in cell wall: | − |
| 15. | Mycolic acid: | − |
| 16. | Quinone series: | MK-7, MK-8 |
| 17. | GC content in bacterial DNA: | 72 mol % |
| 18. | Reduction of nitrate: | + |
| 19. | Denitrogen reaction: | + |
| 20. | Methyl red test: | − |
| 21. | V-P Reaction: | − |
| 22. | Indole generation: | − |
| 23. | Hydrogen sulfide generation: | |
| | In TSI agar: | − |
| | In lead acetate agar: | − |
| 24. | Starch hydrolysis: | + |
| 25. | Utilization of citrate: | |
| | In Koser's culture medium: | − |
| | In Christensen's culture medium: | − |
| 26. | Utilization of inorganic nitrogen source: | |
| | For nitrate salt: | − |
| | For ammonium salt: | Slight |
| 27. | Formation of dye: | + (Yellowish) |
| 28. | Urease: | − |
| 29. | Oxidase: | − |
| 30. | Range of: | |
| | pH: | From 6.0 to 10.0 |
| | Temperature: | From 9 to 42° C. |

-continued

31. Formation of acid:

| | |
|---|---|
| D-Arabinose: | − |
| L-Arabinose: | + |
| D-Xylose: | + |
| D-Glucose: | + |
| D-Mannose: | + |
| D-Fructose: | + |
| D-Galactose: | + |
| Maltose: | + |
| Sucrose: | + |
| Lactose: | + |
| Trehalose: | + |
| D-Sorbitol: | − |
| D-Mannitol: | + |
| Inositol: | − |
| Glycerin: | + |
| Starch: | + |
| Melezitose: | − |
| D-Ribose: | − |

-continued

32. Formation of gas:

| | |
|---|---|
| L-Arabinose: | − |
| D-Xylose: | − |
| D-Glucose: | − |
| D-Mannose: | − |
| D-Fructose: | − |
| D-Galactose: | − |
| Maltose: | − |
| Sucrose: | − |
| Lactose: | − |
| Trehalose: | − |
| D-Sorbitol: | − |
| D-Mannitol: | − |
| Inositol: | − |
| Glycerin: | − |
| Starch: | −. |

\* \* \* \* \*